United States Patent [19]
Anumula et al.

[11] Patent Number: 5,811,246
[45] Date of Patent: Sep. 22, 1998

[54] PROCESS FOR IMMOBILIZATION ONTO THE SURFACES OF ELISA PLATES OF A COMPOUND CARRIER COMPLEX AND FOR IMMUNIZATION

[75] Inventors: Kalyan R. Anumula, King of Prussia, Pa.; Nathan N. Back, Buffalo, N.Y.

[73] Assignee: The Research Foundation of State University of New York, Albany, N.Y.

[21] Appl. No.: 232,412

[22] Filed: Apr. 25, 1994

Related U.S. Application Data

[63] Continuation of Ser. No. 808,603, Dec. 17, 1991, abandoned.

[51] Int. Cl.[6] .................. G01N 33/547; C07K 17/08
[52] U.S. Cl. .................. 435/7.5; 436/532; 436/815; 436/822; 530/811; 530/812; 530/816
[58] Field of Search .................. 435/7.5, 7.9, 7.92, 435/7.94; 436/518, 528, 530, 543, 547, 548, 815, 822, 532; 530/811, 812, 816

[56] References Cited

U.S. PATENT DOCUMENTS

| | | | |
|---|---|---|---|
| 4,496,654 | 1/1985 | Katz et al. | 435/7 |
| 4,656,252 | 4/1987 | Giese | 530/350 |
| 5,001,049 | 3/1991 | Klein et al. | 435/5 |
| 5,106,726 | 4/1992 | Wang | 435/5 |
| 5,120,662 | 6/1992 | Chan et al. | 436/530 |

FOREIGN PATENT DOCUMENTS

| | | |
|---|---|---|
| 0438332A1 | 7/1991 | European Pat. Off. . |
| 0448095A1 | 9/1991 | European Pat. Off. . |
| WO 84/03564 | 9/1984 | WIPO . |
| WO 90/11089 | 10/1990 | WIPO . |
| WO 92/10514 | 6/1992 | WIPO . |

OTHER PUBLICATIONS von Grunigen, R., et al, Biol. Chem. Hoppe–Seyler, vol. 372, pp. 163–172, Mar. 1991 "Enzyme Immunoasssay with Captured Hapten".

World Patents Index Latest Derwent Publications Ltd., London, GB; Database WPIL, accession No. 91–337496, Week 91461 & SU —A—1612264 (Bioorg Chem Inst).

K. Anumula et al., J. Immunological Methods, vol. 135, 199–208, Dec. 31, 1990.

Voller et al. *Manual of Clinical Laboratory Immunology* Chapter 17, pp. 99–109 (1986).

Scott et al. *Molecular Immunology* v. 21 (11) 1055–1060 (1984).

Back et al *FASEB Journal* vol. 2(5) Abstract #4933 (1988).

*Primary Examiner*—Mary E. Ceperley

[57] ABSTRACT

The invention relates to a process for immobilization onto the surface of enzyme linked immunosorbent assay (ELISA) plates of a compound or for immunization with a compound, wherein said compound is in the form of a compound carrier complex which is either an avidin-biotinyl compound complex or a streptavidin-biotinyl compound complex.

19 Claims, 1 Drawing Sheet

PROCESS FOR IMMOBILIZATION ONTO THE SURFACES OF ELISA PLATES OF A COMPOUND CARRIER COMPLEX AND FOR IMMUNIZATION

This is a continuation of application Ser. No. 07/808,603, filed Dec. 17, 1991, now abandoned.

The invention was made under a grant from the United States Government through its National Cancer Institute. The Government has certain rights in this invention.

FIELD OF THE INVENTION

The invention relates to a process for immobilization onto the surfaces of ELISA plates of a compound carrier complex and for immunization.

BACKGROUND OF THE INVENTION

Recent developments in genetic engineering as well as the chemistry of solid phase peptide synthesis have led to the increasingly wider use of synthetic peptides in biochemistry and immunology. Protein sequences which become available as a result of molecular cloning techniques can be synthesized chemically in large quantities for structural, functional, and immunological studies. Peptides corresponding to immunologically important epitopes found on viral and bacterial proteins have also proven to be highly specific reagents which can be used for antibody detection and the diagnosis of infection.

Despite the many advantages synthetic peptides offer, there are a number of disadvantages associated with their use. Because of their relatively short size (generally less than 50 amino acids in length), their structure may fluctuate between many different conformations in the absence of the stabilizing influence of intramolecular interactions present in the full-length protein. Furthermore, the small size of these peptides means that their chemical properties and solubilities will frequently be quite different from those of the full-length protein and that the contribution of individual amino acids in the peptide sequence toward determining the overall chemical properties of the peptide will be proportionally greater.

Many immunological assays require that the antigen used for antibody detection be immobilized on a solid support. Most enzyme-linked immunosorbent assays (ELISA) make use of polystyrene as the solid phase. Many proteins can be stably adsorbed to the solid phase and present sequences which are accessible for subsequent interactions with antibodies. Because of their small size, direct adsorption of peptides to the solid phase frequently gives rise to unsatisfactory results for any of a number of reasons, among which is that the peptide may not possess the correct overall charge or amino acid composition which would enable the peptide to bind to the solid phase.

One way in which binding to the solid phase can be done and made less sensitive to the specific chemical properties of a peptide is by first coupling the peptide to a large carrier molecule. Typically, the carrier molecule is a protein. This approach suffers from the fact that the linkage between the peptide and the carrier protein frequently involves the side chains of internal trifunctional amino acids whose integrity may be indispensable for recognition by antibodies. The binding avidity of antisera for the internally modified peptide is frequently very much reduced relative to the unmodified peptide or the native protein. (see, for example, Briand, J. P., Muller, S., and Van Regenmortel, M.H.V., *J. Immunol. Methods,* 1985, 78:59–69).

The preparation of immuno-reagents to small peptides is carried out traditionally by the immunization of animals with peptide-protein (usually keyhole limpet hemocyanin or bovine serum albumin (BSA)) conjugates (Erlanger, B. F. (1980) The preparation of antigenic hapten-carrier conjugates: A survey. *Methods Enzymol.* 70:85; Harlow E. and Lane D., (1988), In: *Antibodies.* A Laboratory Manual. Cold Spring Harbor Laboratory. Cold Spring Harbor, N.Y., p. 114). A water soluble carbodiimide is often used to mediate the coupling of peptides to protein carriers which results in complex products formed by the amide bonding between —COOH and —NH$_2$ groups available in both the peptides and proteins. This chemical reaction can result in damage to the peptide involved. Small non-physiologic peptides in their free state also can occasionally be used for immunization (Atassi M. Z. (1986), Preparation of monoclonal antibodies to preselected protein regions. Methods Enzymol. 121:69). Unfortunately such procedures are not suitable to raise antibodies against biologically active kinins with very short halflives. Kinins are released in plasma from precursor kininogens by the action of specific kininogenases and degraded rapidly by kininases, including ACE (Miller D. H. and Margolius H. S. (1988) Kallikrein-kininogen-kinin systems. In: L. J. DeGroot and G. F. Cahill. Jr. (Eds.) *Endocrinology,* 2nd edn. Grune and Stratton, Orlando, Fla., p. 2491). Moreover, despite the fact that traditional coupling of small peptides to larger molecular weight antigenic carrier (bovine serum albumin or keyhole limpet hemocyanin) can be successfully used to raise bradykinin (BK) antibodies for immunologic determination of kinins (Ueno A. et al. (1981) Enzyme immunoassay of bradykinin using β-D-galactosidase as a labeling enzyme. *Biochem. Pharmacol.* 30:1659; Odya C. E. et al. (1983) Development of a radioimmunoassay for [Des-Arg$^9$]-bradykinin. *Biochem. Pharmacol.* 32:337; Bedi G. et al. (1985) Monoclonal antibodies to bradykinin inhibit smooth muscle contractile action of bradykinin. *Biochim. Biophys. Acta* 842:90 and Bonner G. et al. (1987) The analytical value for kinin concentration in blood depends on the antiserum used in the bradykinin radioimmunoassay. *J. Clin. Chem. Clin. Biochem.* 25:39), there is the drawback of having possible damage to the peptide as a result of the chemical reaction and of obtaining a higher titer of antibodies directed against the carrier.

SUMMARY OF THE INVENTION

The aim of the invention is to provide a process for preparing a complex compound in which the compound is made immunogenic or in which the complex compound can be immobilized on ELISA plates.

The aim of the invention is to provide a process for immunization with compounds, particularly peptides which are non-immunogenic in the free state, and which cannot be made immunogenic by the classical techniques or for which the classical methods which can be used present the above-mentioned disadvantage.

The aim of the invention is to provide a process for immunization with compounds, which is easy to perform and which can be standardized.

The aim of the invention is to provide a process for immobilization of peptides onto the plastic surface of enzyme-linked immunosorbent assay (ELISA) plates, said peptides being, by themselves, very inefficient coating material.

The various aims of the invention are achieved by a process for immobilization onto the surface of enzyme linked immunosorbent assay (ELISA) plates of a compound or for immunization with a compound, wherein said compound is in the form of a compound carrier complex which is either an avidin-biotinyl compound complex or a streptavidin-biotinyl compound complex.

The invention also relates to a process wherein the compound used for the preparation of the compound carrier complex is a compound containing a free reactive group, preferably a free amino group, and is advantageously a peptide containing a free amino group.

An example of compounds containing a free reactive group can be the anti-cancer compounds adriamycin or amino sugars.

Examples of free reactive groups can be amino, carboxyl, thiol, aldehyde, hydroxyl, imidazole and phenyl.

Examples of peptides containing a free reactive group can be: peptides containing a free thiol group such as peptides containing cysteine, peptides containing aspartic or glutamic acid, peptides containing histidine, peptides containing tyrosine and more preferably peptides containing a free amino group, such as peptides containing a lysine.

According to an advantageous embodiment, the invention also relates to a process for immunization with a peptide wherein the peptide is in the form of a peptide carrier complex which is either an avidin-biotinyl peptide complex or a streptavidin-biotinyl peptide complex.

According to another advantageous embodiment, the peptide carrier complex is such that the peptides comprise from 2 to 100 amino acids, preferably from 5 to 30 amino acids.

An advantageous peptide is bradykinin.

According to an advantageous embodiment of the invention, the peptide involved is not directly linked to biotin, but comprises a spacer arm.

This spacer arm increases the distance between the biotinyl moiety and the peptide, thereby reducing steric hindrance.

Examples of peptide comprising a spacer arm are:
lysyl-bradykinin, methionyl-lysyl-bradykinin, isoleucine-serine-bradykinin or tyrosine-bradykinin.

When lysyl bradykinin is used, the biotin can be condensed either on the $NH_2$-terminal group of the peptide and on the side chain, through the $\epsilon$-$NH_2$ of lysine, using classical processes.

When methionyl-lysyl-bradykinin is used, the biotin can be condensed on the terminal $NH_2$ of the peptide and on the $\epsilon$-$NH_2$ of the lysyl residue, using classical processes.

When isoleucine-serine-bradykinin is used, the biotin is condensed on the $NH_2$-terminal of the peptide.

When tyrosine is used, the biotin is condensed on the $NH_2$-terminal of the peptide.

The invention also relates to a process for preparing antibodies having a titer of at least 250, and more particularly of at least 20 comprising immunizing an animal with a compound carrier complex of the invention, and recovering the serum portion of the blood of said immunized animals.

The titer is with respect to the compound, and not the titer with respect to the compound carrier complex, which comprises antibodies directed against avidin and streptavidin.

The titer is the reciprocal of the dilution which gives a positive reaction. "Positive reaction" means any reaction which is equal to or greater than the average plus two times the standard deviation of the reaction obtained on at least five negative samples.

The titer can be determined as follows:
consecutive two-fold dilutions are made of the antiserum to be tested; these dilutions are then tested to determine the highest dilution which still gives a positive reaction; the reciprocal of this dilution is then calculated to give the titer of antiserum.

The invention also relates to a process wherein the amount of complex used is of at least 25 $\mu$g, preferably of 2.5 mg, to obtain a titer of about 20.

To obtain the antibodies directed against the compound, the complex can be given to the animal all at once, or can be given in multiple injections (for instance 5 injections of 0.05 mg) with the total amount of complex being of 2.5 mg.

A larger quantity of compounds can be used, for instance when the immunization scheme comprises several doses of complex of 2.5 mg. The complex may also be administered together with an adjuvant for the purpose of improving the antibody response.

The invention also relates to monoclonal antibodies, such as prepared according to the process of the invention.

The invention also relates to a process for immobilization of a peptide onto the surface of ELISA plates wherein the peptide used is in the form of a peptide carrier complex which is either an avidin-biotinyl peptide complex or a streptavidin-biotinyl peptide complex.

The invention also relates to a process for determining the amount of a peptide comprising:
coating the peptide on the surface of ELISA plates in the form of a complex of avidin-biotinyl peptide or of streptavidin-biotinyl peptide, thus obtaining a coated complex;
allowing antibodies against peptide to react with the coated complex;
detecting the amount of antibodies which have reacted with the peptide;
calculating the amount of peptide.

The invention also relates to a process for determining the amount of a peptide comprising:
coating the peptide on the surface of ELISA plates in the form of a streptavidin-biotinyl peptide complex or avidin-biotinyl peptide complex, thus obtaining a coated complex;
allowing antibodies against streptavidin-biotinyl peptide complex (if the plates are coated with avidin-biotinyl peptide complex) or against avidin-biotinyl peptide complex (if the plates are coated with streptavidin-biotinyl peptide complex), to react with the coated complex, thus excluding the binding of avidin or streptavidin antibodies;
detecting the amount of antibodies which have reacted with the above-mentioned complex;
calculating the corresponding amount of peptide.

The invention also relates to a process for determining the amount of a peptide comprising:
coating the peptide on the surface of ELISA plates in the form of a complex of avidin-biotinyl peptide or of streptavidin-biotinyl peptide, thus obtaining a coated complex;
allowing antibodies against avidin-biotinyl peptide complex or against streptavidin-biotinyl peptide complex, respectively free from avidin (or from streptavidin) cross-reacting antibodies, to react with the coated complex;
detecting the amount of antibodies which have reacted with the above-mentioned complex;
calculating the corresponding amount of peptide.

The antibodies against avidin- (or streptavidin-) biotinyl peptide complex can be obtained according to the process of the invention.

This process also implies the presence of avidin (streptavidin) cross-reacting antibodies. In order to remove these avidin (streptavidin) cross-reacting antibodies, the antibodies can be precipitated with an excess of avidin (streptavidin).

The invention also relates to a process for determining the amount of antibodies directed to a peptide in a serum comprising:

coating the peptide on the surface of ELISA plates in the form of a complex of avidin-biotinyl peptide or of streptavidin-biotinyl peptide, thus obtaining a coated complex;

allowing antibodies against peptide to react with the coated complex;

detecting the amount of antibodies which have reacted with the peptide.

The invention also relates to a process for determining the amount of antibodies directed to a peptide in a serum comprising:

coating the peptide on the surface of ELISA plates in the form of a streptavidin-biotinyl peptide complex or avidin-biotinyl peptide complex, thus obtaining a coated complex;

allowing antibodies against streptavidin-biotinyl peptide complex (if the plates are coated with avidin-biotinyl peptide) or against avidin-biotinyl peptide (if the plates are coated with streptavidin-biotinyl peptide), to react with the coated complex, thus excluding the binding of avidin or streptavidin antibodies;

detecting the amount of antibodies which have reacted with the above-mentioned complex.

The invention also relates to a process for determining the amount of antibodies directed to a peptide in a serum comprising:

coating the peptide on the surface of ELISA plates in the form of a complex of avidin-biotinyl peptide or of streptavidin-biotinyl peptide, thus obtaining a coated complex;

allowing antibodies such as obtained according to the invention, free from avidin (or streptavidin) cross-reacting antibodies, to react with the coated complex;

detecting the amount of antibodies which has reacted with the above-mentioned complex.

The invention also relates to a process for preparing a biotinylated compound comprising:

mixing a compound containing a free reactive group with an appropriate amount of biotinylating agent so that the reactive group of the compound reacts with biotinylating agent.

The invention also relates to a process for preparing a compound carrier complex comprising:

mixing a compound containing a free reactive group with an appropriate amount of biotinylating agent so that the reactive group of the compound reacts with biotinylating agent;

adding an appropriate amount of avidin or streptavidin.

When the free reactive group is an amino group, the biotinylating agent can be the following:

biotin-N-hydroxysuccinimide ester, biotinyl-ε-aminocaproic acid-N-hydroxy-succinimide ester, sulfosuccinimidyl 6-(biotin-amido)hexanoate, N-hydroxysuccinimide-iminobiotin, sulfosuccinimidyl 2-(biotin-amido)-ethyl-1,3'dithiopropionate.

When the free reactive group is a thiol group, the biotinylating agent can be the following:

biotinyl-bromoacetyl hydrazide, 3-(N-maleimido-propionyl)biocytin.

When the compound, particularly the peptide, contains aspartic or glutamic acid, the biotinylating agent can be biotin hydrazide.

When the free reactive group is an aldehyde, the biotinylating agent can be biocytin hydrazide.

When the compound, particularly the peptide contains histidine or tyrosine, the biotinylating agent can be p-diazobenzoyl biocytin.

FIG. 1 represents the titration of bradykinin antisera collected at various times during the production of rabbit antibodies against the avidin-biotinyl-peptide complex. Effect of time on antisera dilution to give 1.0 absorbance unit (inset).

On the first larger scale curves, the absorbance (at 492 nm) is plotted against the antisera dilution ($10^{-3}$).

On the smaller scale curves, the antisera titer ($10^{-3}$) is plotted against the number of months after injection. For the purposes of this experiment only, and in order to facilitate comparison of the sera, the titer has been defined as the antibody dilution which results in an optical density of 1.000 in the test system used, since this optical density falls within the linear portion of the titration curves.

DETAILED DESCRIPTION OF THE INVENTION

EXAMPLES

Figure 1:
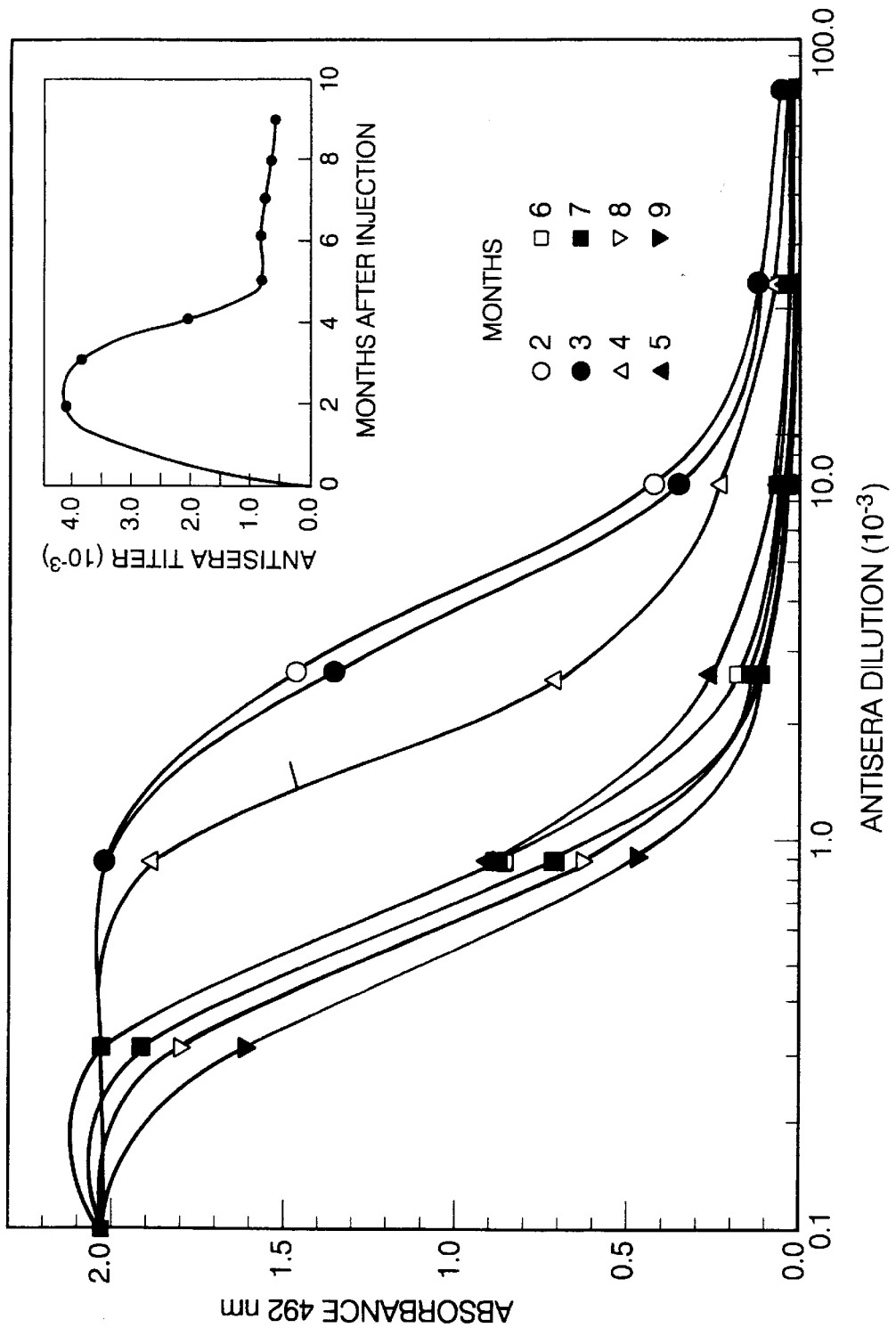

Avidin, biotinyl-ε-aminocaproyl-N-hydroxy succinimide were purchased from Sigma Chemical Co. (St. Louis, Mo.). Affi-Gel 10 was purchased from Bio-Rad (Richmond, Calif.). Bradykinin, lysyl-BK, methionyl-lysyl-BK, isoleucine-serine-BK, tyrosine-BK, des-arginine$^9$-BK, [tyrosine$^8$]-BK, [tyrosine$^5$]-BK were obtained either from Chemical Dynamics (South Plainfield, N.J.) or Sigma Chemical Co. Polystyrene ELISA plates were from Laboratory Products Sales (Rochester, N.Y.). Bovine serum albumin (BSA) and γ-globulins (95–99% pure) were obtained from Sigma Chemical Co. Goat anti-rabbit and anti-mouse immunoglobulin-horseradish peroxidase conjugates were available from Zymed Laboratories (South San Francisco, Calif.). TPCK-treated trypsin was a product of Worthington Biochemical Corp. (Freehold, N.J.) and 1,10-phenanthroline was obtained from J. T. Baker Co. (Phillipsburg, N.J.). Benzamidine hydrochloride, EDTA and N-ethylmaleimide (NEM) were products of Sigma Chemical Co. BSA-BK conjugate was prepared as described earlier (Bedi G. and Back N. (1985) Monoclonal antibodies to bradykinin inhibit smooth muscle contractile action of bradykinin. *Biochim. Biophys. Acta* 842:90). Normal rat plasma was obtained in citrate (0.38%) from Pel-Freeze (Rogers, A. K.) or prepared from blood collected from the abdominal aorta of anesthetized rats. Plasma from turpentine treated (0.5 ml/100 g) rats was collected after 48 h. Human plasma was prepared from freshly collected blood. Kininogen was purified from rat plasma using a papain affinity column followed by DEAE-Tris-acryl column chromatography (Anumula K. R. et al. (1989) Quantitative determination of kinins released by trypsin using enzyme-linked immunosorbent assay (ELISA) and identification by high-performance liquid chromatography (HPLC). *Biochem. Pharmacol.* 38:2421).

Preparation of avidin-biotinyl-aminocaproyl-peptide complex

For immunization of the rabbit, an avidin-biotinyl-aminocaproyl-peptide complex was prepared by mixing avidin with biotinylated lysyl-bradykinin (Lys-BK). Biotinylation of Lys-BK was carried out in 0.1M NaHCO$_3$ in 30% acetonitrile by reaction of Lys-BK (final concentration of the peptide was 0.2–0.3 mg/ml) with an equimolar amount of biotinyl-ε-aminocaproyl-N-hydroxy succinimide ester (1 mg/ml in acetonitrile, stock). The reaction was allowed to proceed at ambient temperature for 16 h. The reaction mixture was diluted with an equal volume of 2× saline and the avidin (containing four binding sites/mol) was added in a molar ratio of 1:4. The final preparation contained 0.1 mg of BK/ml of the complex form.

Antiserum preparation and affinity purification of BK-antibodies

A mixture of anti-BK mouse monoclonal antibodies D6A5, B6C9 and A3D9, previously prepared with defined specificity (Bedi G. et al. (1985) Monoclonal antibodies to bradykinin inhibit smooth muscle contractile action of bradykinin. *Biochim. Biophys. Acta* 842:90) was compared against the polyclonal antibodies prepared as described below.

Antibodies against BK were raised in a New Zealand albino rabbit (2.5–3.0 kg). Avidin-biotinyl-BK complex (representing 50 μg of peptide) in 0.5 ml was emulsified with 4.0 ml of complete Freund's adjuvant and injected subcutaneously into multiple dorsal sites. Four weeks later, a similar suspension prepared with incomplete Freund's adjuvant representing 25 μg of peptide complex was injected intramuscularly. Booster injections were administered at 2 and 8 months. Blood was collected from the ear vein at 2 months and each month thereafter to the 9th month. The antisera was separated by centrifugation and stored at 4° C. overnight to be used for titer estimation and antibody purification.

BK antibodies were purified by affinity chromatography on a column of BK covalently bound to Sepharose-4B. The affinity column was made accordingly; Affi-Gel 10 (1.5 ml in 4 ml suspension) was washed on a sintered glass funnel with 10 ml isopropanol, followed by a 10 ml water wash. The moist gel was added to a solution of BK (2.0 mg) in 2 ml 0.1M NaHCO$_3$. Remaining gel particles were rinsed into the BK solution with an additional ml of NaHCO$_3$. The suspension was shaken end-over-end for 16 h at ambient temperature. The remaining active ester groups on the gel were masked by treatment with 0.1M glycine, pH 8.5, for 4 h. BK-Affigel 10, 1.5 ml, was poured into a 2.5 ml syringe column and washed with 5 bed vols. of 0.9% NaCl in 10 mM Tris-HCl, pH 7.4. The uncoupled BK recovered in the wash was estimated by ELISA.

The BK affinity column, containing 1.15 mg of immobilized BK per ml of resin, was equilibrated with 0.9% NaCl in 50 mM sodium phosphate, pH 7.4 (PBS) containing the protease inhibitors benzamidine hydrochloride (10 mM), EDTA (5 mM), 1,10-phenanthroline (5 mM) and NEM (1 mM). 4 ml antisera were diluted with an equal volume of 2× PBS containing inhibitors and applied to the column at ambient temperature. The column was washed with 10 bed vols. of equilibration buffer followed by 5 vols. of PBS, pH 8.5. Antibodies were eluted with PBS, pH 11.0, and the antibody solution neutralized with dilute acetic acid. During the course of the study, BSA was added (final concentration 1.0 mg/ml) to the antibody solution before storage at 0°–4° C.

Tryptic digestion of plasma

Kinins were released from purified rat kininogen and from plasma by treatment with TPCK-treated trypsin as previously described (Anumula K. R. et al. (1989) Quantitative determination of kinins released by trypsin using enzyme-linked immunosorbent assay (ELISA) and identification by high-performance liquid chromatography (HPLC). *Biochem. Pharmacol.* 38:2421). Briefly, 50–100 μl of rat or human plasma was treated with acidic 2-propanol at 100° C. for 10 min and the protein precipitate incubated for 60 min with 0.5 mg of trypsin in 0.3 ml of 50 mM sodium phosphate, pH 8.0, containing 0.15M NaCl, 5 mM EDTA and 2 mM 1,10-phenanthroline. The trypsin then was inactivated by boiling for 10 min and, after centrifugation, an aliquot of the supernatant was used to estimate the BK by ELISA.

Determination of kinins by ELISA

ELISA was carried out by a method recently developed for kinins (Anamula K. R. et al. (1989), see above) based on the established procedures (Voller A. et al. (1986) Enzyme linked immunosorbent assay. In: N. R. Rose, H. Friedman and J. L. Fahey (Eds.), *Manual of Clinical Laboratory Immunology*, 3rd edn. American Society for Microbiology, Washington, D.C., p. 17). Polystyrene plates were coated with appropriate dilutions of one of the following materials so as to obtain 1.0 absorbance unit in the non-competing wells: avidin-biotinyl-BK complex, and BSA-BK conjugates. Non-specific binding sites were blocked with 1% BSA in PBS-Tween 20 buffer containing the inhibitor 1,10-phenanthroline.

Incubations at 37° C. for 1 h were carried out in the coated plates, first with the monoclonal or polyclonal BK antibodies and then with the second antibody-horseradish peroxidase conjugate. To reduce the non-specific binding of the antibody reagents, 0.1% of each of BSA and γ-globulins was added to the buffer. Color was developed at ambient temperature with o-phenylnediamine/H$_2$O$_2$ until the desired intensity was reached (25–30 min). The reaction then was stopped with H$_2$SO$_4$ (¼ dilution) and the color intensity measured at 492 nm with a Titertek Multiskan microwell plate reader from Flow Laboratories (McLean, Va.).

Preparation of peptide (BK, LBK) conjugated reagents

Biotinylation of BK was through an active ester of biotiny-ε-aminocaproic acid in a typical reaction of amide synthesis (Anderson G. W. et al. (1964) The use of esters of N-hydroxysuccinimide in peptide synthesis. *J. Am. Chem. Soc.* 86:1839). (Lys-BK was an advantageous kinin because it provides an extra NH2 group/mol of kinin. This should improve the efficiency of the coupling of kinin moiety to the biotin derivative. In the avidin-biotinyl-BK complex the ε-aminocaproic acid moiety combines with the aliphatic side chain of the biotin, thereby situating the peptide away from the large avidin protein portion. This spacing gives the peptide enough conformational freedom to interact properly with the antibody.

The peptide conjugates were excellent coating materials for ELISA plates and for studying the comparative binding characteristics of monoclonal and polyclonal antibodies as described below.

Raising polyclonal antibodies

Biotinylated bradykinin bound to avidin was used to raise antibodies in the rabbit. Avidin binds 4 mol of biotin with a high affinity of $10^{-15}$M (Green N. M. et al. (1975) Avidin. In: C. B. Anfinsen, J. T. Edsell and F. M. Richards (Eds.), *Advances in Protein Chemistry*, vol. 29. Academic Press, New York, p. 85). Avidin-biotinyl-peptide complex as such, when injected, produced a high titer antibody in the rabbit. The bradykinin-antibody reactivity, as determined by ELISA, in the sera collected at various immunization time intervals, can be seen. Two months after the initial immunization, an antisera dilution of 1/4000 was required in the ELISA (PLS-BK coating concentration 1/12,000) to obtain an absorbance of 1.0 U with the horseradish peroxidase/OPD/H$_2$O$_2$ system. The antibody titer steadily decreased with time and at six and nine months the dilution required was 1/750 and 1/400, respectively. Booster shots with PLS-BK conjugates did not increase the BK antibody titer. The sensitivity of the ELISA for the determination of BK did not change during the course of antibody production. The rabbit also produced antibodies to avidin but the titer was not determined. The avidin cross-reacting antibodies were removed from the antisera by precipitation with excess avidin. BK antibodies remaining in the supernatant had the same binding characteristics in the ELISA as the non-avidin-precipitated antisera.

During the purification of the rabbit antibodies by Affi-Gel 10-bound BK affinity chromatography, approximately 150 μg of the antibody protein was bound per ml of affinity gel as determined in the fraction eluted with pH 11.0 buffer. Monoclonal antibodies under similar purification conditions showed poor column binding since only negligible amounts of antibody appeared in the pH 11.0 PBS buffer eluted fraction. Activity of the affinity purified antibodies was more stable than the antisera.

ELISA with avidin-biotinyl-BK complex

In addition to the use of the avidin-biotinyl-BK complex as an antigen, the peptide complex was compared against the BSA-BK conjugate as a coating material in the ELISA with monoclonal antibodies. It can be seen that responses with the avidin-biotinyl-BK complex as coating were more favorable than with the BSA-BK conjugate at equivalent dilutions indicating a higher retention of antibody on the avidin-complex coated plates. Since bradykinin alone was found to be a very inefficient coating material, it was not used in the present ELISA procedure. In contrast, less than 0.2 μg BK/ml of the avidin-biotin-BK complex was sufficient for determination of BK.

CONCLUSIONS

For the first time such an avidin-biotinyl-peptide complex was shown to be a very good antigen for raising antibodies.

The avidin-biotinyl-peptide complex also was an efficient immobilizing agent on plastic surfaces as demonstrated by ELISAs in which the mouse anti-BK monoclonal antibodies (MAb) were used. Only 0.2 μg of BK/ml of BK complex was required in the assay. Free BK could not be used for coating the plastic plates in the determination of BK by these ELISA procedures.

We claim:

1. A process for immobilization onto the surface of enzyme linked immunosorbent assay plates a peptide comprising the step of coating said peptide on the surface of said plates wherein said peptide is in the form of a peptide carrier complex which is either an avidin-biotinyl peptide complex or a streptavidin-biotinyl peptide complex.

2. A process according to claim 1, wherein said peptide is a peptide containing a free reactive group.

3. A process for determining the amount of a peptide in an unknown sample comprising the steps of:
   (a) coating the peptide on the surface of ELISA plates in the form of a complex of an avidin-biotinyl peptide or of a streptavidin-biotinyl peptide, to produce a coated complex;
   (b) allowing antibodies against said peptide to react with said coated complex;
   (c) detecting the amount of antibodies which have reacted with said peptide; and
   (d) calculating the amount of said peptide.

4. A process for determining the amount of a peptide in an unknown sample comprising the steps of:
   (a) coating the peptide on the surface of ELISA plates in the form of a streptavidin-biotinyl peptide complex or an avidin-biotinyl peptide complex, to produce a coated complex;
   (b) allowing antibodies against said streptavidin-biotinyl peptide complex, if the plates are coated with avidin-biotinyl peptide complex, or against said avidin-biotinyl peptide complex if the plates are coated with streptavidin-biotinyl peptide complex, to react with said coated complex, thus excluding the binding of avidin or streptavidin antibodies;
   (c) detecting the amount of antibodies which have reacted with said complex; and
   (d) calculating the corresponding amount of said peptide.

5. A process for determining the amount of a peptide in an unknown sample comprising the steps of:
   (a) reacting the sample peptide with a reagent to form an avidin-biotinyl peptide complex or a streptavidin-biotinyl peptide complex;
   (b) coating the peptide on the surface of ELISA plates in the form of an avidin-biotinyl peptide complex or a streptavidin-biotinyl peptide complex to produce a coated complex;
   (c) allowing antibodies against said avidin-biotinyl peptide complex or said streptavidin-biotinyl peptide complex free from avidin or from streptavidin cross-reacting antibodies, to react with said coated complex;
   (d) detecting the amount of antibodies which have reacted with said coated complex; and
   (e) calculating the corresponding amount of said peptide.

6. A process for determining the amount of antibodies directed to a peptide in a serum comprising the steps of:
   (a) coating the peptide on the surface of ELISA plates in the form of a complex of an avidin-biotinyl peptide or of a streptavidin-biotinyl peptide, to produce a coated complex;
   (b) allowing antibodies against said peptide to react with said coated complex; and
   (c) detecting the amount of antibodies which have reacted with said peptide.

7. A process according to claim 2 wherein the peptide is a peptide containing a free amino group.

8. A process according to claim 2 wherein the peptide, is bradykinin, lysylbradykinin, methionyl-lysyl-bradykinin, isoleucine-serine-bradykinin or tyrosine-bradykinin.

9. A process according to claim 2 where said peptide comprises from 5 to 30 amino acids.

10. A process for immobilization onto the surface of enzyme linked immunosorbent assay plates a peptide comprising the step of coating onto the surface of said plates an avidin-biotinyl-BK complex.

11. A peptide-carrier complex immobilized to a solid support, said carrier being either avidin-biotin or streptavidin-biotin.

12. A peptide-carrier complex according to claim 11, wherein said peptide is 5 to 30 amino acids in length.

13. A peptide-carrier complex according to claim 11 wherein said peptide comprises bradykinin.

14. A peptide-carrier complex according to claim 11 wherein said peptide comprises one peptide selected from the group consisting of bradykinin, lysyl-bradykinin, methionyl-lysyl-bradykinin, isoleucine-serine-bradykinin and tyrosine-bradykinin.

15. A peptide-carrier complex of claim 13 wherein said complex further comprises a spacer arm which links said peptide and carrier.

16. A peptide-carrier complex of claim 11 wherein said spacer arm is selected from the group consisting of lysyl, methionyl-lysyl, isoleucine-serine and tyrosine.

17. A peptide-carrier complex according to claim 11 wherein said solid support is a surface of an ELISA plate.

18. A peptide-carrier complex according to claim 11 wherein said solid support is a polystyrene.

19. A peptide-carrier complex according to claim 11 wherein said solid support is a plastic surface.

* * * * *